United States Patent [19]

Yoneda et al.

[11] Patent Number: 5,594,512
[45] Date of Patent: Jan. 14, 1997

[54] OPHTHALMOLOGICAL PHOTOGRAPHING INSTRUMENT

[75] Inventors: Yutaka Yoneda; Hiroyuki Ohtsuka, both of Tokyo, Japan

[73] Assignee: Kabushiki Kaisha Topcon, Tokyo, Japan

[21] Appl. No.: 558,194

[22] Filed: Nov. 15, 1995

[30] Foreign Application Priority Data

Nov. 16, 1994 [JP] Japan .................................. 6-281629

[51] Int. Cl.⁶ .............................. A61B 3/14; A61B 3/10; G03B 29/00
[52] U.S. Cl. ............................ 351/206; 351/221; 396/18
[58] Field of Search ................................. 351/205, 206, 351/208, 211, 213; 354/62

[56] References Cited

U.S. PATENT DOCUMENTS 5,181,055  1/1993  Sano et al. ......................... 351/206 X Primary Examiner—Huy Mai
Attorney, Agent, or Firm—Finnegan, Henderson, Farabow, Garrett & Dunner, L.L.P.

[57] ABSTRACT

An ophthalmological photographing instrument for fluorescent photograph comprising a device for irradiating illuminating light to a fundus of an eye to be tested, a device for projecting target luminous light to the eye, an image receiving device capable of receiving a reflection image of the target luminous flux reflected by the eye together with an image of the fundus of the eye, and observation/photographing means for receiving and photographing an image of the eye received by the image receiving device, wherein the ophthalmological photographing instrument further comprises a moving picture recording device into which the received image output coming from the image receiving device is input, a timer for counting time which has elapsed since the time when a fluorescent agent for the use of the fluorescent photograph has been injected into a vein, and a quenching device for reducing or quenching the target luminous flux after the passage of a predetermined time from the time when the injection of the fluorescent agent has been made, based on an output of the timer.

8 Claims, 5 Drawing Sheets

OPHTHALMOLOGICAL PHOTOGRAPHING INSTRUMENT

BACKGROUND OF THE INVENTION

This invention relates to an improvement of an ophthalmological photographing instrument which has irradiation means for irradiating illuminating light to the fundus of an eye to be tested, projection means for projecting a target luminous flux to the fundus of the eye, and image receiving means for receiving a reflection image of a target image luminous flux reflected by the eye together with an image of the fundus of the eye, and in which, based on output of the images received by the image receiving means, the eye is observed/photographed and the eye can be photographed under a fluorescent light.

Heretofore, there are known as recording systems which can be employed in an ophthalmological instrument, a still image recording system using a film and an electronic picture recording device as recording media, and a moving image recording system using an electronic picture recording device (for example, VTR or the like) as a recording medium. There are known, as photographing systems which can be employed in an ophthalmological instrument, a visible color photographing system, a visible fluorescent light photographing system, an infrared fluorescent light photographing system and the like. The fluorescent photographing technology is utilized for a diagnostic check of a circulating state of blood flowing in the blood vessels of the eye fundus. As one effective recording system for it, the moving image recording system receives much attention. Lately, the moving image recording system has been increasingly employed with the further improvement of the performance of electronic picture recording devices.

The ophthalmological instrument includes, in order to avoid incorrect photograph, an alignment projection system for projecting an alignment target to the eye in order to align the instrument body with the eye, and a focusing projecting system for projecting a split target to the eye fundus, which serves as a target for adjusting a focusing state of the eye fundus.

Those targets are projected to the eye fundus or cornea. Therefore, if an eye fundus image should be received as it is, it could happen that a desired eye fundus part is impossible to be recognized because those target images are transferred together with the eye fundus image and the target images are superimposed on the eye fundus image.

In the case of a still image recording, it is made possible by extinguishing or blocking a target luminous flux only when a recording is carried out that the target image is not transferred when the image of the eye fundus is recorded. However, in the case of a moving image recording, it is practically impossible to extinguish or block the target image luminous flux only when a recording is made because a picture recording is constantly made. Since those target images are transferred together with the eye fundus image, they are superimposed on the eye fundus image. As a consequence, it gives rise to the inconvenience that a desired eye fundus part is impossible to be recognized.

It can be contemplated not to project those target images when a moving image is recorded. However, this is practically impossible to be applied to the case of a fluorescent photograph, because when a fluorescent photograph is made, a fluorescent eye fundus image is unobtainable for a time interval from a few seconds to a few dozens of seconds which are required for a fluorescent agent to reach the blood vessels in the eye fundus and the examiner is compelled to observe the eye fundus in the dark during that time interval. As a consequence, it is impossible to recognize whether or not the instrument body is correctly aligned with the eye and whether or not the eye fundus image is well focused. It is only after the fluorescent eye fundus image is obtained that the incorrect alignment and incorrect focusing are confirmed. Thus, there is a fear that an attempt to photograph an initial fluoresent fundus image is failed.

SUMMARY OF THE INVENTION

It is, therefore, an object of the present invention to provide an ophthalmological photographing instrument in which when a moving image is recorded and when a fluorescent photograph is made, target images can be prevented from being superimposed on an eye fundus image and an attempt to correctly photograph an initial eye fundus fluorescent image can be prevented from being failed.

In order to achieve the above object, an ophthalmological photographing instrument for fluorescent photograph as defined in claim 1 comprises a device for irradiating illuminating light to a fundus of an eye to be tested, a device for projecting target luminous light to the eye, an image receiving device capable of receiving a reflection image of the target luminous flux reflected by the eye together with an image of the fundus of the eye, and observation/photographing means for observing and photographing an image of the eye received by the image receiving device, wherein the ophthalmological photographing instrument further comprises a moving picture recording device into which the received image output coming from the image receiving device is input, a timer for counting time which has elapsed since the time when a fluorescent agent for the use of the fluorescent photograph has been injected into a vein, and a quenching device for reducing or quenching the target luminous flux after the passage of a predetermined time from the time when the injection of the fluorescent agent has been made, based on an output of the timer.

According to the ophthalmological photographing instrument as defined in claim 1, the irradiating means irradiates an illuminating light to the fundus of an eye to be tested. The projecting means projects a target luminous flux to the eye. The image receiving means can receive a reflection image of the target luminous flux coming from the eye together with the eye fundus image. A received image output from the image receiving means is input into the moving image recording means. The timer means counts time which has elapsed since the time when a fluorescent agent for the use of a fluorescent photograph has been injected into the vein. The quenching means reduces or quenches the target luminous flux after the passage of a predetermined time from the time when the fluorescent agent has been injected into the vein based on the output from the timer means.

DETAILED DESCRIPTION OF THE EMBODIMENTS

Figure 1:
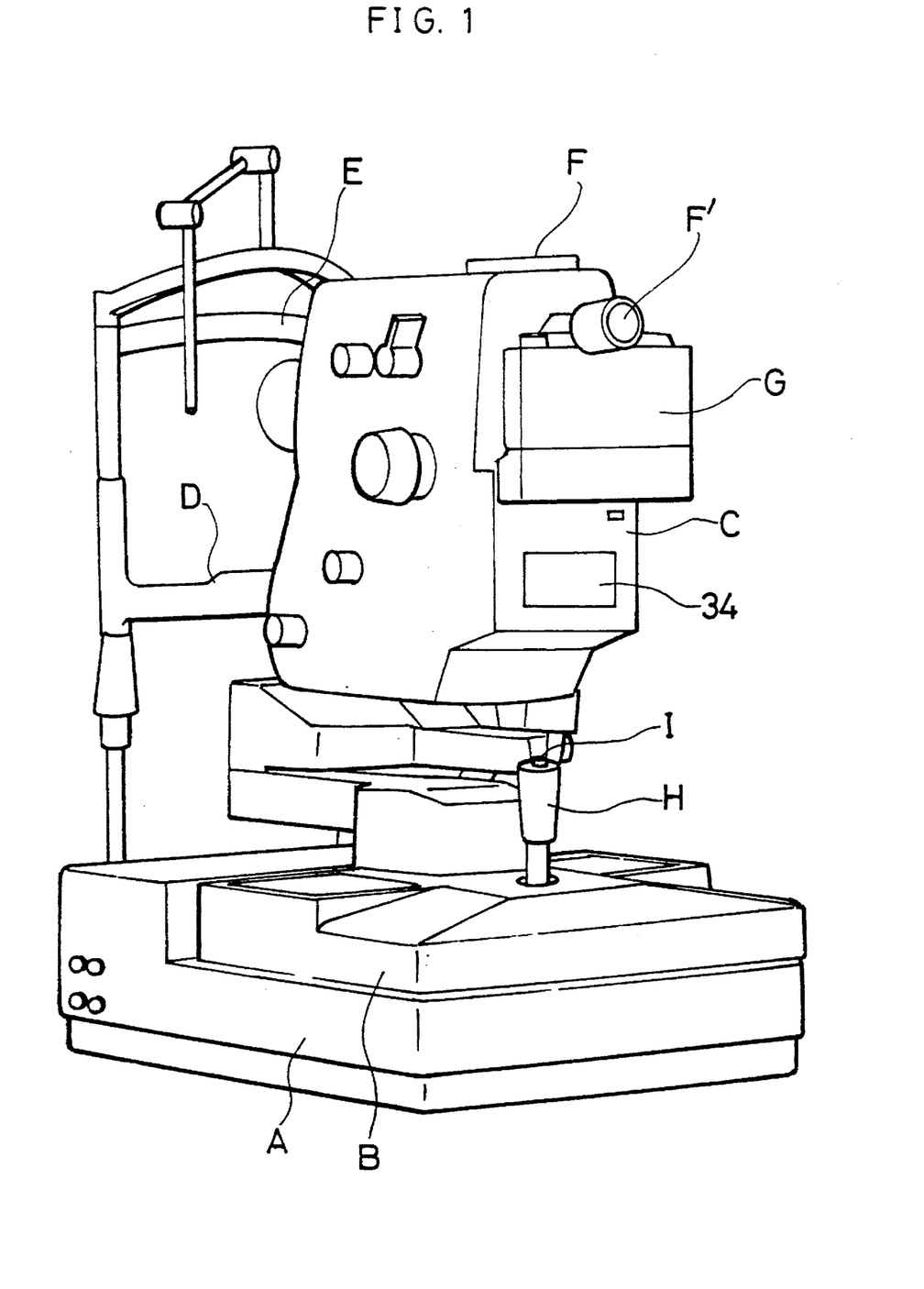
FIG. 1 is a perspective view showing an outer appearance of an ophthalmological photographing instrument according to one embodiment of the present invention.

FIG. 1 is a perspective view showing an outer appearance of an ophthalmological photographing instrument according to one embodiment of the present invention. In this FIG. 1, reference character A denotes a base; B, a cradle; C, an instrument body; D, a chin retainer; E, a forehead abutment; F, a TV camera attaching portion; G, a 35 mm film camera; H, a joy stick; and I, a photographing button, respectively. Those component parts are all known per se.

Figure 2:
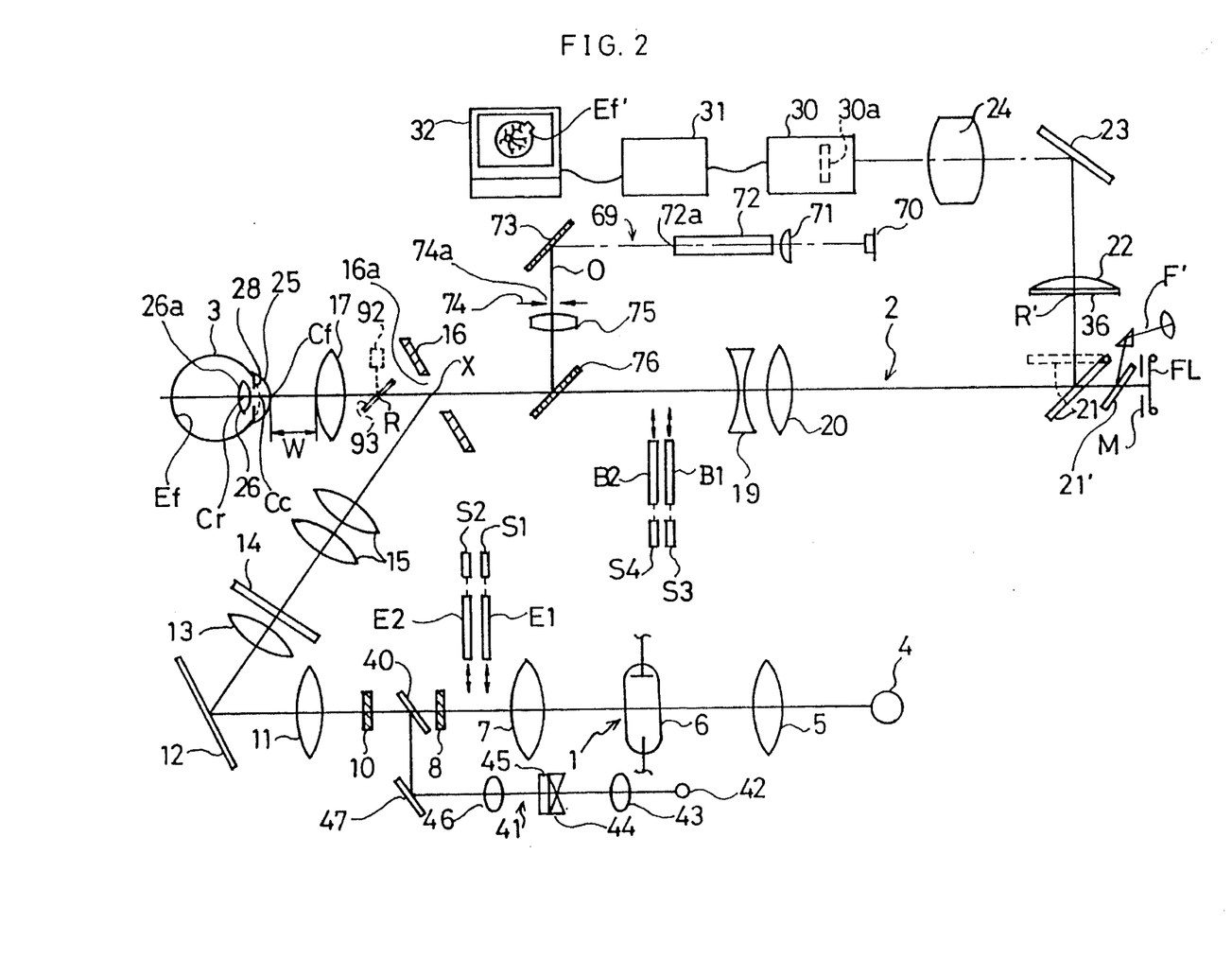
FIG. 2 is an optical diagram for the ophthalmological photographing instrument of FIG. 1.

Optical systems shown in FIG. 2 are disposed within the instrument body C. In FIG. 2, reference numeral 1 denotes an illuminating optical system of the ophthalmological photographing instrument; 2, a photographing optical system; and 3, an eye to be tested, respectively. The illuminating optical system 1 generally comprises such optical parts as a halogen lamp 4 as an illuminating light source to be used for observation, a condenser lens 5, a xenon tube 6 as an illuminating light source to be used for photographing, a condenser lens 7, illuminating diaphragms 8, 10, a relay lens 11, a reflecting mirror 12, a relay lens 13, a sunspot plate 14, a relay lens 15, a perforated mirror 16, an objective lens 17 and the like. An observing/photographing illuminating light from the halogen lamp 4 is irradiated to an eye fundus Ef through the optical parts from the condenser lens 5 to the objective lens 17. A photographing illuminating light from the xenon lamp 6 is irradiated to the eye fundus Ef through the optical parts from the condenser lens 7 to the objective lens 17. A visible fluorescent exciter filter E1 and an infrared fluorescent exciter filter E2 are removably inserted into an optical path of the illuminating optical system 1 between the condenser lens 7 and the illuminating diaphragm 8. Reference alphabetical numeral S1 denotes a solenoid for driving the exciter filter E1, and S2, a solenoid for driving the exciter filter E2, respectively. The illuminating diaphragm 8 is conjugate with a cornea 25 and the other illuminating diaphragm 10 is conjugate with a rear surface 26a of a crystal body 26. The sunspot plate 14 is a shading member for prohibiting a reflecting light from the surface of the objective lens 17 from passing through a perforation portion 16a of the perforated mirror 16. In FIG. 2, reference numeral 28 denotes a pupil.

A small mirror 40 is disposed on an optical path between the illuminating diaphragm 8 and the illuminating diaphragm 10 of the illuminating optical system 1. This small mirror 40 constitutes a part of a focusing target projecting system 41. The focusing target projecting system 41 includes a splitting light source 42 as a focusing light source, a condenser lens 43, a split prism 44, a target plate 45, a relay lens 46, and a reflecting mirror 47. The construction of the focusing target projecting system 41 is known per se. When the splitting light source 42 is turned on, infrared luminous flux collected by the condenser lens 43 is guided to the split prism 44. Then, the infrared luminous flux passed through the split prism 44 is allowed to pass through a window, not shown, of the target plate 45 to become a split target luminous flux. This split target luminous flux is then guided to the relay lens 46, the reflecting mirror 47, and the small mirror 40. The split target luminous flux reflected by the small mirror 40 is projecting to the eye fundus Ef of the eye 3 via the optical parts from the illuminating diaphragm 10 to the objective lens 17. As a consequence, A split target image resembling the window of the target plate 45 is formed on the eye fundus Ef.

The photographing optical system 2 includes the objective lens 17 facing the eye 3, the perforated mirror 16, a focusing lens 19, an imaging lens 20 and a quick return mirror 21. This quick return mirror 21 constitutes a part of an electronic observing/photographing system. The construction of the electronic observing/photographing system will be described later. A half mirror 76 is disposed on the optical path of the observing/photographing optical system 2 between the perforated mirror 16 and the focusing lens 19. A visible fluorescent barrier filter B1 and an infrared fluorescent barrier filter B2 are removably inserted into the optical path between the half mirror 76 and the focusing lens 19. Reference alphabetical numeral S3 denotes a solenoid for driving the visible fluorescent barrier filter B1, and S4, a solenoid for driving the infrared fluorescent barrier filter B2, respectively. A quick return mirror 21' and a shutter M and a film FL which constitute a part of a 35 mm film camera G are disposed behind the quick return mirror 21. The quick return mirror 21' constitutes a part of a finder optical system F'.

The half mirror 76 constitutes a part of an alignment projecting system 69. This alignment projecting system 69 includes an alignment light source 70, a condenser lens 71, a light guide 72, a slant mirror 73, a double perforated diaphragm 74, and a relay lens 75. The alignment light source 70 generates light having a wavelength ranging from a visible area to an infrared area. An alignment target luminous flux, which has been made incident to the light guide 72, is output from its outgoing end 72a, reflected by the slant mirror 73 toward the double perforated diaphragm 74 so as to pass through the two perforation portions 74a (only one is shown) and guided to the half mirror 76 via the relay lens 75. The alignment target luminous flux reflected by the half mirror 76 toward the perforated mirror 16 is temporarily imaged as an alignment target image on a central position X of the perforation portion 16a. A pair of alignment target luminous fluxes temporarily imaged on the central position X of the perforation portion 16a are then projected to the cornea 25 of the eye 3 through the objective lens 17. When a working distance W from the eye 3 to the instrument body C and a vertical and horizontal position with respect to the eye 3 are correct, an alignment target image is projected by the pair of alignment target luminous flux for forming an image of the outgoing end 72a to a ½ position Cc of the curvature of the cornea which is an intermediate position between the vertex Cf of the cornea 25 and the center Cr of curvature of the cornea 25. When the working distance W from the eye 3 to the instrument body C is displaced from the correct position, an alignment image based on a pair of alignment luminous flux is projected in a separated form with reference to the ½ position Cc of the curvature of the cornea 25. That is, when the working distance from the eye 3 to the instrument body C is displaced from the correct position, the double perforated diaphragm 74 plays a role as an optical member for projecting the alignment target image based on the alignment target luminous flux to the eye 3 in its separated form.

When the working distance W is correct, the alignment target luminous flux reflected by the cornea 25 is imaged, by the objective lens 17, on a position R conjugate with the eye fundus Ef. The alignment reflecting target luminous flux, which has been imaged on the position R, is allowed to pass through the perforation portion 16a and then guided to a TV camera as image receiving means as later described in the same manner as the reflecting luminous flux for forming the image of the eye fundus. In observation during a visible color photograph, a light spot as the alignment target image is displayed on a screen of a television monitor as later described, together with the eye fundus image Ef'. When the working distance W is displaced from the correct position, the light spot is displayed in the screen of the television monitor in its separated form, so that the examiner can make an alignment by checking whether the alignment images are coincided or separated.

The electronic observing/photographing system includes a field lens 22, a reflecting mirror 23, a TV relay lens 24, and a television camera 30 as image receiving means. Reference numeral 30a denotes an image receiving surface of the television camera 30. The television camera 30 is connected to an electronic picture recording device 31 such as a VTR, an optical disk or the like. The recording device 31 is connected to a monitor 32. The electronic picture recording device 31 plays a role as the moving image recording means. A control circuit 100 functions as means for judging whether or not the recording mode is a moving image recording mode and as means for judging whether or not the photographing mode is a fluorescent photographing mode.

Figure 3:
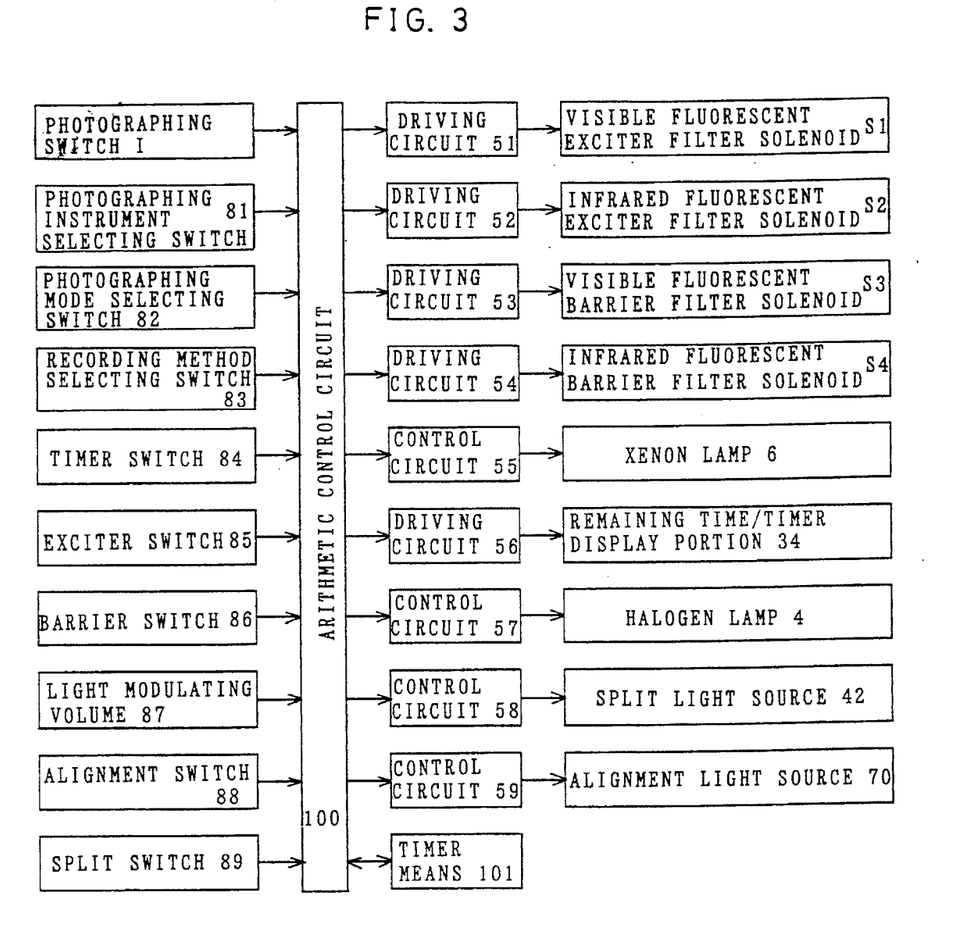
FIG. 3 is a control circuit diagram of the ophthalmological photographing instrument of FIG. 1.

This ophthalmological photographing instrument includes an arithmetic control circuit 100 shown in FIG. 3. An input side of the arithmetic control circuit 100 is connected to a photographing switch I, a photographing instrument selecting switch 81, a photographing mode selecting switch 82, a recording method selecting switch 83, a timer switch 84, an exciter switch 85, a barrier switch 86, a light modulating volume 87, an alignment switch 88, and a split switch 89. An output side of the arithmetic control circuit 100 is connected to driving circuits 51 to 59. The driving circuit 51 is connected to a solenoid S1; the driving circuit 52, to a solenoid S2; the driving circuit 53, to a solenoid S3; the driving circuit 54, to a solenoid S4; the control circuit 55, to the xenon lamp 6; the control circuit 56, to a display portion 34; the control circuit 57, to the halogen lamp 4, the control circuit 58, to the splitting light source 42; and the control circuit 57, to an alignment light source 70, respectively.

The photographing switch I has a role for lightening the xenon lamp 6. The photographing instrument selecting switch 81 is used for selecting one of the 35 mm camera G, a polaroid camera (not shown), a TV camera, etc. as an electronic picture recording device so as to be used as a recording medium. The photographing mode selecting switch 82 is used for selecting one of a color photographing mode, a visible mono-color photographing mode, a visible fluorescent photographing mode, a infrared mono-color photographing mode, etc. so as to be used as a photographing mode. The recording method selecting switch 83 is used for selecting one of a still image recording mode and a moving image recording mode. When the still image recording mode has been selected by the recording method selecting switch 83, the control circuit 100 has a role for turning off the split light source 40 and the alignment light source 70 in the ON-state of the xenon lamp 6 through actuation of the photographing switch I.

The timer switch 84 is used for driving timer means 101. Upon actuation of the timer switch 84, the timer means 101 starts the counting from zero. The display portion 34 is normally in a counter display state in which the number of photograph is displayed. When a moving image recording mode has been selected through the recording method selecting switch 83 and the timer switch 84 has been actuated, the control circuit 100 switches the display portion 34 from the counter display state to a remaining time display state in which the remaining time until the turning off of the target mark is displayed. The remaining time can be displayed by graph, numeric figures, etc. The display portion 34 is disposed on the instrument body C but it may also be disposed on the cradle portion B.

The exciter switch 85 is used for driving the solenoids S1 and S2. The barrier switch 86 is used for driving the solenoid switches S3 and S4. The arithmetic control circuit 100 drive and controls the solenoids S1 and S3 when the photographing mode selecting switch 82 is in the visible fluorescent photographing mode and drives and controls the solenoids S2 and S4 when the photographing mode selecting switch 82 is in the infrared fluorescent photographing mode. As a consequence, an exciter filter corresponding to the photographing mode is inserted into the optical path of the illuminating optical system 1 and the remaining exciter filters are retreated from the optical path or they are maintained in the retreating position. A barrier filter according to the photographing mode is inserted into the optical path of the photographing optical system 2 and the remaining barrier filters are retreated from the optical path or they are maintained in the retreating position. The light modulating volume 87 is used for adjusting the brightness of the halogen lamp 4.

Next, operation of the embodiment of the ophthalmological photographing instrument according to the present invention will be described.

The operation hereinafter described in detail is for the infrared fluorescent photographing mode and for both the still image recording mode and the moving image recording mode.

(Still Image Recording Mode)

A TV camera is selected by the photographing instrument selecting switch 81, an infrared fluorescent photographing mode is selected by the photographing mode selecting switch 82 and a still image recording mode is selected by the recording method selecting switch 83. Upon depression of the exciter switch 85, the control circuit 52 is driven and the infrared fluorescent exciter filter E2 is inserted into the optical path of the illuminating optical system 1 by the solenoid S2. By observing the alignment target image and the focusing target image in the monitor 32, the vertical and horizontal positional adjustment of the instrument body C with respect to the eye 3 is performed and a focusing in the optical axis direction is performed.

Figure 4:
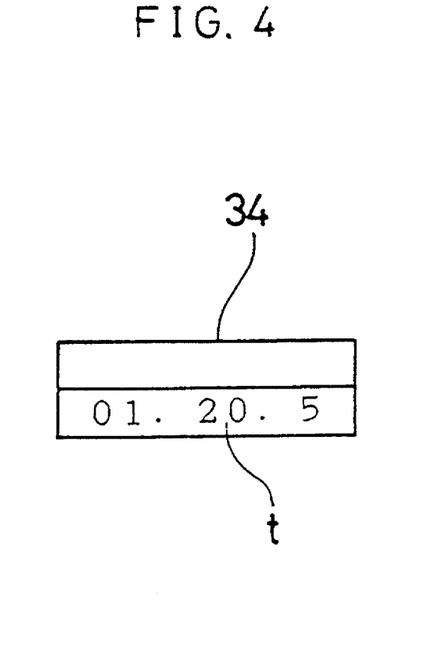
FIG. 4 is a schematic view of a display portion for the ophthalmological photographing instrument of FIG. 1, displaying time which has elapsed since the time when a fluorescent agent has been injected into the vein.

Subsequently, a fluorescent agent is injected into the vein of the patient and at the same time, the timer switch 84 is depressed. Then, the timer means 101 starts actuation. As shown in FIG. 4, the time t which has elapsed from the time when the fluorescent agent has been injected into the vein is displayed in the display portion 34. Upon depression of the barrier switch 86, the control circuit 54 is driven and the infrared fluorescent barrier filter B2 is inserted into the optical path of the photographing optical system 2 by the solenoid S4. Then, a light quantity for observing the eye fundus is adjusted by using the light modulating volume 87. Then, a fine positional adjustment of the instrument body C with respect to the eye 3 and a fine adjustment of focusing are performed by the alignment target/focusing target while observing the monitor 32.

When the photographing switch I is turned on, the arithmetic control circuit 100 drives the control circuit 55 to light the xenon lamp 6 in order to photograph the eye fundus. During the time the xenon lamp 6 is in the ON-state, the arithmetic control circuit 100 turns off the split light source 40 and the alignment light source 70. Accordingly, the respective target images are not recorded in superimposed relation with the fluorescent image.

(Moving Image Recording Mode)

The TV camera 30 is selected by the photographing instrument selecting switch 81, an infrared fluorescent photographing mode is selected by the photographing mode selecting switch 82 and a moving image recording mode is selected by the recording method selecting switch 83. Upon depression of the exciter switch 85, the control circuit 52 is driven, and the infrared fluorescent exciter filter E2 is inserted into the optical path of the illuminating optical system 1 by the solenoid S2. The recording device 31 is turned on to start the moving image recording operation. By observing the alignment target image and the focusing target image in the monitor 32, the vertical and horizontal positional adjustment of the instrument body C with respect to the eye 3 is performed and a focusing in the optical axis direction is performed.

Figure 5:
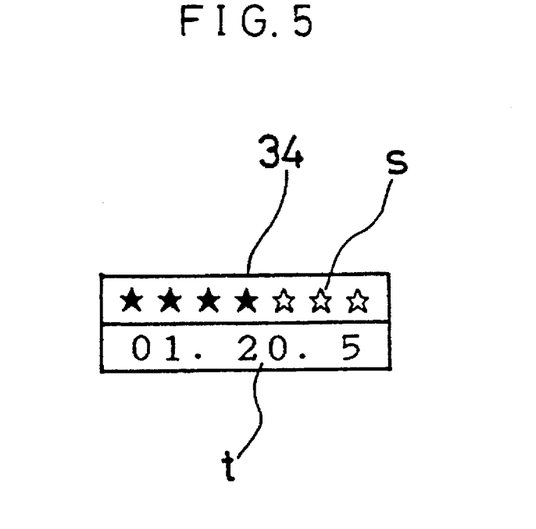
FIG. 5 is a schematic view of a display portion for the ophthalmological photographing instrument of FIG. 1, displaying time which has elapsed since the time when a fluorescent agent has been injected into the vein and the remaining time required for turning off the target luminous flux.

Subsequently, a fluorescent agent is injected into the vein of the patient and at the same time, the timer switch 84 is depressed. Then, the timer means 101 starts actuation. As shown in FIG. 5, the time t which has elapsed from the time when the fluorescent agent has been injected into the vein is displayed in the display portion 34. At the same time, the remaining time until the target image is turned off is displayed as a visual data S. Upon depression of the barrier switch 86, the control circuit 54 is driven and the infrared fluorescent barrier filter B2 is inserted into the optical path of the photographing optical system 2 by the solenoid S4. Then, a light quantity for observing the eye fundus is adjusted by using the light modulating volume 87. Then, a fine positional adjustment of the instrument body C with respect to the eye 3 and a fine adjustment of focusing are performed by the alignment target/focusing target while observing the monitor 32.

After the passage of a predetermined time, the target image is turned off by the control circuit 100. After the target image has been turned off, a fine positional adjustment of the instrument body C with respect to the eye 3 and a fine adjustment of focusing are performed while observing the fluorescent image in the monitor 32. Accordingly, although an eye fundus image with a target image reflected thereon is obtained until the time a fluorescent image is obtained, the respective target images are not recorded in superimposed relation with the fluorescent image after the fluorescent image is obtained. That is, the control circuit 100 also functions as quenching means.

Although the present invention has been described in the form of preferred embodiments, the invention is by no means limited to the embodiments. For example, the time required until the time the target mark is turned off may be changed, the target mark may be turned on again in accordance with necessity after the target mark is once turned off, and the target mark may be prohibited from being turned off.

In this embodiment, the target mark is turned off with reference to time. In the alternative, the target mark may be turned off with reference to the output level of the fluorescent image.

Figure 6:
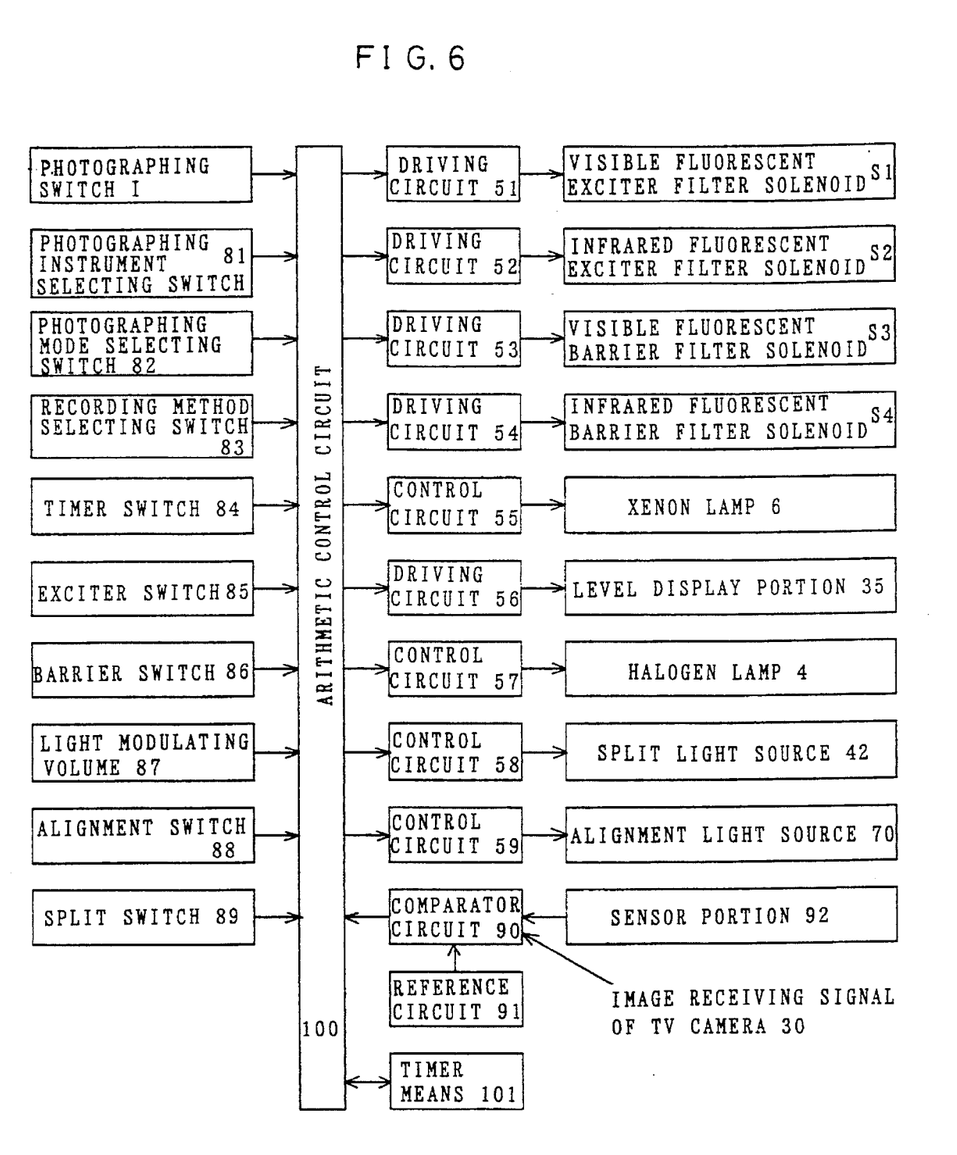
FIG. 6 is a control circuit diagram for an ophthalmological photographing instrument according to another embodiment of the present invention.

For example, as shown in FIG. 2, there can be employed an arrangement in which a small mirror 93 as indicated by a broken line is provided on a part of the photographing optical system 2, a reflecting image from the eye fundus Ef is received by a sensor 92 which constitutes a part of the brightness detecting means, and a reference value of a reference circuit 91 is compared with a value of brightness of a sensor 92 by a comparator circuit 90 so that the target image is turned off when the brightness of the fluorescent image exceeds a predetermined level (see FIG. 6). Also, the target image may be turned off by comparing the image receiving output from the TV camera 30 with the reference value.

Since the ophthalmological photographing instrument as defined in claim 1 of the present invention is constructed in the manner as mentioned above, the target images can be prevented from being transferred to the eye fundus image when a fluorescent photograph is performed and an initial attempt for correctly photographing an eye fundus image can be prevented from being failed.

What is claimed is:

1. An ophthalmological photographing instrument for fluorescent photograph comprising irradiating means for irradiating illuminating light to a fundus of an eye to be tested, projecting means for projecting target luminous light to the eye, image receiving means capable of receiving a reflection image of the target luminous flux reflected by the eye together with an image of the fundus of the eye, and observation/photographing means for observing and photographing an image of the eye received by said image receiving means, wherein said ophthalmological photographing instrument further comprises:

moving picture recording means into which the received image output coming from said image receiving means is input; timer means for counting time which has elapsed since the time when a fluorescent agent for the use of the fluorescent photograph has been injected into a vein, and quenching means for reducing or quenching the target luminous flux after the passage of a predetermined time from the time when the injection of the fluorescent agent has been made, based on an output of said timer means.

2. An ophthalmological photographing instrument according to claim 1, further comprising judging means for judging whether or not the mode for photographing is a fluorescent photographing mode, and judging means for judging whether or not the mode for recording is a moving picture recording mode, when the mode for photographing is a fluorescent photographing mode and the mode for recording is a moving picture recording mode, the target luminous flux being reduced or quenched after the passage of a predetermined time from the time when the injection of the fluorescent agent has been made.

3. An ophthalmological photographing instrument according to claim 1, further comprising brightness detecting means for detecting brightness of a fluorescent image coming from the fundus of the eye, said quenching means for reducing or quenching the target luminous flux when a fluorescent photographing mode has been selected, when said timer has made a counting and when the brightness of the fluorescent image coming from the fundus of the eye has exceeded a predetermined level.

4. An ophthalmological photographing instrument for fluorescent photographing comprising irradiating means for irradiating illuminating light to a fundus of an eye to be tested, projecting means for projecting target luminous light to the eye, image receiving means capable of receiving a reflection image of the target luminous flux reflected by the eye together with an image of the fundus of the eye, and observation/photographing means for observing and photographing an image of the eye received by said image receiving means, wherein said ophthalmological photographing instrument further comprises:

moving picture recording means into which the received image output coming from said image receiving means is input; timer means for counting time which has elapsed since the time when a fluorescent agent for the use of the fluorescent photograph has been injected into a vein, and quenching means for reducing or quenching the target luminous flux when the received image output which had been input into said moving picture recording means or a picture signal output from said moving image recording means has exceeded a predetermined level.

5. An ophthalmological photographing instrument according to claim 1, further comprising a display portion for displaying time which has elapsed since the fluorescent agent has been injected.

6. An ophthalmological photographing instrument according to claim 2, wherein a photographing switch for recording a still image also serves as at least one of means for lightening, extinguishing and reducing the target luminous light when a moving image is recorded.

7. An ophthalmological photographing instrument according to claim 1, further comprising time changing means for changing the time required for actuating said quenching means.

8. An ophthalmological photographing instrument according to claim 1, further comprising a switch for lightening, extinguishing or reducing the target luminous flux through a manual operation made by an examiner.

* * * * *